United States Patent
Rosenthal

(10) Patent No.: US 6,703,412 B1
(45) Date of Patent: Mar. 9, 2004

(54) METHOD OF TREATING SLEEPLESSNESS WITH MELATONIN ON AN ACUTE BASIS

(76) Inventor: Holly A. Rosenthal, 11 Pine Glen, Blauvelt, NY (US) 10913

( * ) Notice: Subject to any disclaimer, the term of this patent is extended or adjusted under 35 U.S.C. 154(b) by 0 days.

(21) Appl. No.: 10/255,255

(22) Filed: Sep. 27, 2002

(51) Int. Cl.$^7$ .............................................. A61K 31/40
(52) U.S. Cl. ........................ 514/416; 514/419; 514/923
(58) Field of Search ................................ 514/416, 419, 514/923

(56) References Cited

U.S. PATENT DOCUMENTS

| | | | | |
|---|---|---|---|---|
| 4,600,723 A | * | 7/1986 | Short et al. .................. | 514/416 |
| 4,665,086 A | * | 5/1987 | Short et al. .................. | 514/416 |
| 5,242,941 A | * | 9/1993 | Lewy et al. .................. | 514/416 |
| 5,449,683 A | | 9/1995 | Wurtman ..................... | 514/419 |
| 5,498,423 A | * | 3/1996 | Zisapel ........................ | 424/464 |
| 5,641,801 A | | 6/1997 | Wurtman ..................... | 514/419 |
| 6,214,377 B1 | * | 4/2001 | Dittgen et al. ............... | 424/462 |

OTHER PUBLICATIONS

2001 "Sleep in America" Poll, Mar. 2001; www.sleepfoundation.org.
NHTSA What is the Mission of Drowsy Driving Program!; www.nhtsa.dot.gov/people/injury/drowsy$_{13}$ driv9ing1/index.html (partially posted Sep. 5, 2001).
Mediamark Research Study 2000; www.mediamark.com/MRI/ps/psHlT002.cfm.
Zhdanova, et al: Melatonin: A Sleep–Promoting Hormone; Sleep 20(10) 899–907, 1997.
Lewy et al: Melatonin shifts Human Circadian Rhythms According to a Phase–Response Curve; Chronobiology International vol. 9, No. 5, pp. 380–392, 1992.
Aldous et al: Plasma concentrations of melatoonin in man following oral absorption of different preparations; Br. J. clin. Pharmac. (1985), 19, 517–521.
Waldhauser, et al: sleep laboratory investigations on hypnotic properties of melatonin; Psychopharmacology (1990) 100: 222–226.
Barchas, et al: Acute Pharmacology of Melatonin; Nature vol. 214, May 27, 1967, pp. 919–920.
Voordouw, et al: Melatonin and Melatonin–Progestin Combinations Alter Pituitary–ovarian Functionin Women and Can Inhibit Ovulation; J. Clinical Endocrinology and metabolism Vo. 74, No. 1, 108–117, 1992.
Hughes, et al: Sleep–Promoting anf Hypoythermic effects of daytime melatonin Administration in Humans; Sleep 20(2): 124–131, 1997.
Attenburrow, et al: Low dose melatonin improves sleep in healthy middle–aged subjects; Psychopharmacology (1996) 126: 179–181.
Wurtman, et al.: Improvement of sleep quality by melatonin; The Lancet, vol. 346, Dec. 2, 1995, p. 1491.
James, et al: Melatonin Admininstration in Insomnia; Neuropsychopharmacology 1990 vol. 3, No. 1, pp 19–23, 1989.
Cagnacci: Melatonin in relation to physiology in adult humnans; J Pineal Res 1996: 21: 200–213.
Dawson, et al: The hypothermic effect of melatonin on core body temperature: Is more better?; J. Pineal Res 1996: 20:192–197.
Sack, et al: Use of melatonin for sleep and circadian rhythm disorders; Ann Med 1998; 40: 115–121.
Wirz–Justice, et al: Melatonin: Nature's Soporific?; J Sleep Res (1996) 5, 137–141.
Sack, et al: Sleep–Promoting effects of melatonin: At What Dose, in Whom, Under What Conditions, and by What mechanisms?; Sleep 20(10): 908–913, 1997.
Nave, et al: residual effects of daytime administration of melatonin on performance relevant to flight; Behavioural Brain research 131 (2002) 87–95.
Lushington, et al: Daytime Melatonin Administration in elderly Good and Poor Sleepers: Effects of Core Body Temperature and Sleep latency: Sleep 20(12): 1135–1144, 1997.
Tzischinsky, et al: Melatonin Possesses time–Dependent Hypnotic Effects; Sleep 17(7): 638–645, 1994.
Dollins, et al: Effect of pharmacological daytime doses of melatonin on human mood and performance; Psuchpharmacology (1993) 112: 490–496.
Dollins, et al: Effect of inducing nocturnal serum melatonin concentrations in daytime on sleep, mood, body temperature, and performance; Proc. Natl. Acad. Sci. USA vol. 91, pp. 1824–1828, Mar. 1994.
Rogers, et al: Effect of daytime oral melatonin administration on neurobehavioral performance in humans; J Pineal Res. 1998: 25: 47–53.
Suhner, et al: Impact of Melatonin on Driving Performance; J Travel Med 1998, 5:7–13.
Lieberman, et al: Effects of Melatonin on Human Mood and Performance; Brain Research 323 (1984) 201–207.
Dawson, et al: Melatonin and sleep in humans; J Pineal Res 1993; 15:1–12.
von Gizycki, et al: The effect of Melatonin on Performance in a Visual Vigilance Task; Sleep research 26, 1997, p132.
Slotten, et al: Does melatonin Have an effect on cognitive Performance?; Psychoneuroendocrinology, vol. 21, No. 8, pp. 673–680, 1996.

(List continued on next page.)

Primary Examiner—Frederick Krass
(74) Attorney, Agent, or Firm—Irving M. Fishman

(57) ABSTRACT

A method of treating sleeplessness in a human comprising administering to said human suffering from said sleeplessness an effective sleep-inducing amount of not greater than about 5 mg of melatonin or a pharmaceutically acceptable salt thereof, said administration being at a point in time after said human attempts to go to sleep until no less than one hour prior to said patient's desired awakening time.

15 Claims, No Drawings

OTHER PUBLICATIONS

Hughes, et al: The Role of Melatoninand Circadian Phase in Age–Related Sleep–maintenance Insonimia. Assessment in a Clinical Trial of Melatonin Replacement; Sleep vol. 21, No. 1, 1998, pp. 52–68.

Sack, et al: Melatonin as a Chronobiotic Drug: DN&P 9(6), Jul. 1, 996, pp. 325–332.

Arendt, et al: The Effects of Chronic Small Doses of Melatonin Given in the Late Afternoon on fatigue in Man: A Preliminary Study; Neuroscience letters, 45 (1984) 317–321.

Caldwell: The Use of Melatonin: An Information Paper; Aviation, Space, and Environmental medicine, vol. 71, No. 3, Mar. 2000, pp. 238–244.

Karasek, et al : Future of melatonin as a therapeutic agent; neuroendocrinology Letters 2002; 23 (suppl 1):118–121.

Vakkuri, et al: Oral Administration and Distribution of Melatonin in Human Serum, saliva and Urine; Life Sciences, vol. 37, pp. 489–495, 1985.

Waldhauser, et al: Bioavailability of oral Melatonin in Humans; Neuroendocrinology 39: 307–313 (1984).

Zhdanova, et al: Efficacy of Melatonin as a Sleep–Promoting Agent; Journal of Biological Rhythms, vol. 12, No. 6, pp. 644–650, 1997.

* cited by examiner

METHOD OF TREATING SLEEPLESSNESS WITH MELATONIN ON AN ACUTE BASIS

CROSS-REFERENCE TO RELATED APPLICATIONS

Not Applicable

STATEMENT REGARDING FEDERALLY SPONSORED RESEARCH OR DEVELOPMENT

Not Applicable

FIELD OF THE INVENTION

The present invention relates to treatment of common forms of sleeplessness and the use of limited dosage regimens using melatonin therefor.

BACKGROUND OF THE INVENTION

According to the National Sleep Foundation's 2002 "Sleep in America" Poll among 1004 US adults, almost seven in ten (69%) of adults experience one or more sleep problems at least a few nights a week. Furthermore, about three in ten (29%) say they experience insomnia every or almost every night. Amongst the most common forms of insomnia are awakening during the night or waking up too early and not being able to get back to sleep (experienced by 32% and 24% of adults at least a few nights per week respectively) These forms of sleeplessness are in fact more prevalent than the inability to initially fall asleep (experienced by 23% of adults).The result is that 40% of adults are so sleepy during the day that it interferes with their ability to perform their daily activities a few days per week or more, according to the study. 53% say they have driven while drowsy, with 19% admitting to have actually dozed off during driving. The National Highway Safety Administration estimates that 100,000 automobile accidents, 40,000 injuries, and 1,550 fatalities annually are related to drowsy driving.

Despite the prevalence and consequences of sleeplessness problems, the NSF study indicates that only 6% of adults take prescription sleep medications, with an equal percentage taking OTC sleep remedies a few nights a month or more. In fact, Mediamark Research Inc.'s 2000 Study among over 25,000 US adults indicates that only 4.6% have used any nonprescription sleep aid within the last six months. It is conjectured that non-treatment of this serious problem is due at least in part to the "mis-fit" between currently available non-prescription treatment options and the specific sleep problems suffered by many adults. Specifically, whereas more adults suffer from middle of the night or early morning awakening, all currently available sleep aids direct users to take the sleep medication before initially going to sleep.

In doing so, the individual must elect to take a medication for a problem—the inability to initially fall asleep—which they do not have, since most insomnia sufferers have no problem in initially falling asleep. Furthermore, they must elect to take medication before knowing whether they will or will not experience sleeplessness later during the sleep period (since the majority do not experience premature awakening on a daily basis.) In other words, all available sleep remedies do not address the more prevalent sleep problems and require dosage before knowing if the problem will be experienced at all.

An additional issue keeping insomnia sufferers from taking OTC medications are concerns about grogginess associated with the hypnotics, sedatives and antihistamines currently available for the treatment of sleeplessness. It is these properties that in fact prohibit the usage of such remedies at any time later than before the initial bedtime.

Melatonin (N-acetyl-5-methyoxytryptamine) is a neurohormone produced by the pineal gland and screted at night, reaching levels 10–40 times higher than those present in the daytime. It is lipid-soluble and released into the bloodstream and cerebrospsinal fluid as it is synthesized. The highest levels of melatonin are found in children age 5 and under, after which levels begin to decline (Zhdanova I., Lynch H,; and Wurtman R., Sleep; 1997; 20:899–907)

It has been established that endogenous melatonin onset occurs sometime after 1700 with peak levels between 0100 and 0500, and with offset occurring around 0700 or 0800. According to the phase response curve indicated by Lewy and associates ("*Melatonin shifts human circadian rhythms according to a phase response curve*" Chronobiolology Intl 1992; 9:380–92) melatonin administered at around 0200 would neither advance nor delay the circadian rhythm. Melatonin taken after that time is likely also to have minimal effects on circadian rhythms since it has been shown to phase advance better than phase delay.

Melatonin has a short biological half-life, ranging from 32–48 minutes for 2–100 mg. doses and is rapidly metabolized by the liver. (Aldhous, M., et. al.: *Plasma Concentrations of Melatonin in Man Following Oral Absorption of Different Preparations*. Br. J. Clin. Pharm.1985; 19:517–521) Doses of melatonin from very small (0.1 mg.) to huge (2 g.) have been administered to humans with no serious side effects. According to Waldhauser, Saletu and Trinchard-Lugan in "*Sleep Laboratory Investigations on Hypnotic Properties of melatonin*" (Psychopharmacology; 1990: 100:222–6), "The dose response curve for melatonin's effect on sleep is clearly different from those of currently recognized hypnotic agents. As the dose of benzodiazepine or barbiturate is increased, increasing degrees of sleepiness and eventually coma result. In contrast, melatonin doses of several grams, given to humans, can raise blood levels to concentrations that are over 1,000 times physiological levels, but never produce involuntary loss of consciousness. Indeed, some people may not even become overly sleepy."

Melatonin is regarded as non-toxic since an $LD_{50}$ has not been determined. An early study of the toxicity of melatonin failed to produce death in mice given 800 mg ·kg $-^1$ (Barchas J, DaCosta F., and Spector. "*Acute Pharmacology of Melatonin*. Nature 1967; 214:919–20) One study reports that ingestion of 300 mg of melatonin daily, for four months, resulted in inhibition of ovulation in women. (Bettie C. G. et. al., J. Clin. Endocrin. Metabol. 1992;74:108–117).

The physiological effects of melatonin appear to be the regulation of the circadian biological timing system and modulation of sleep, acting on sleep propensity and core body temperature. The sleep-promoting properties of melatonin are well documented for both daytime and night time use. (Hughes, Badia: "*Sleep Promoting and Hypothermic Effects of Daytime Melatonin Administration in Humans*. Sleep 1997;20:124–31; Attenburrow, Cowen, Sharpley, "*Low Dose Melatonin Improves Sleep in Healthy Middle-Aged Subjects*. Psychopharmacology 1996; 126:179–81; Wurtman, Zhdanova. "*Improvement of Sleep Quality by Melatonin*" Lancet 1995;346:1491 and many other studies) In "Melatonin Administration in Insomnia" (James, Sack, Rosenthal, Mendelson, Neuropsychopharmacology 1990; 3:19–23) no sleep-related benefits are observed, however it has been argued that this is due to a "sleep ceiling effect"

problem, in which sleep efficiency in the placebo condition is 91%, enabling little opportunity for improvement in the treatment condition.

One of the effects of melatonin is to reduce core body temperature, although the exact method of action is unknown (Cagnacci A., J. "*Melatonin in Relation to Physiology in Adult Humans*" Pineal Res: 1996; 21:200–13). However, the fact that melatonin impacts body temperature is important since many researchers believe melatonin may regulate the sleep/wake cycle through thermoregulatory mechanisms. It has been found that the decline in core body temperature occurs around the same time as the rise in melatonin, and that the increase in core body temperature coincides with melatonin decreases. As the dose of melatonin increases, a more reliable decrease in body temperature occurs. In a study by Dawson, Gibbon and Singh ("*The Hypothermic Effects of Melatonin on Core Body Temperature: Is More Better?*" J. Pineal Res. 1996; 20:192–7) where 0.1, 0.5, 1 and 5 mg. of melatonin were administered at 1600, lower doses produced more variability in the temperature decrease, whereas higher doses produced less variability in both time and amount of temperature decrease. Low doses of melatonin (producing blood levels within the normal physiological nighttime range) have been studied in connection with the ability to reduce the time period for onset of sleep, and a dosage of less than 1 mg as a single dose has been patented by Wurtman et al in U.S. Pat No. 5,641,801 and U.S. Pat. No. 5,449,683.

The impact of low doses of melatonin may have played a role in blunting the sleep-promoting impact of a middle of the night dosage of 0.5 mg of melatonin in Hughes, Sack, Lewy "*The Role of Melatonin and Circadian Phase in Age-Related Sleep-Maintenance Insomnia*", Sleep 1998;21:52–68),. The investigators speculate that the minimal temperature reduction from the low dosage was not sufficient to produce sleep effects. Attenburrow, Cowen and Sharpley report in "*Low Dose Melatonin Improves Sleep in Healthy Middle Aged Adults*" (Psychopharmacology 1996;126:179–81 that 1.0 mg., but not 0.3 mg, given prior to bedtime significantly increased total sleep time and efficiency. It also should be noted that the methodology used in the Hughes study was to wake subjects in the middle of the night to take medication. This protocol (which was executed to compare multiple dosing with a controlled release dose) does not mimic the in-vivo condition of spontaneous awakening prior to the desired awakening time. There is no indication that any of the subjects spontaneously awakened during the test execution nor that they regularly suffer from middle of the night awakenings.

Sack, Lewy and Hughes ("*Use of Melatonin for Sleep and Circadian Rhythm Disorders*". Ann Med 1998; 30:115–21) and Wirz-Justice ("*Melatonin: Nature's Soporific?*. J. Sleep Res. 1996; 5:137–41) claim that melatonin acts as a soporific (allowing sleep to occur) rather than as a hypnotic (forcing sleep to occur). Importantly, the sleep promoting effects of melatonin are predicted to be minimal at times when the sleep drive has been discharged, as argued by Sack, Hughes, Edgar and Lewy ("*Sleep Promoting Effects of Melatonin*". Sleep 1997; 20:908–15). This may explain why in "*Residual Effects of Daytime Melatonin Performance Relevant to Flight*" (Nave, Iani, Herer, Gopher, Lavie, Behav. Brain Res. 2002;131:87–95) melatonin did not depress alertness or activation, and actually improved performance and activation in some test measurements vs. placebo when administration of 3 mg. of melatonin was followed by a two hour nap. Similarly, in "*Daytime Melatonin Administration in Elderly Good and Poor Sleepers*" (Lushington, Pollard, Lack, Kennaway, and Dawson Sleep 1997;20:1135–44), the impact of melatonin was modest, perhaps related to the test protocol which called for 11 sleep test opportunities during the test day which ran from 900 to 2000 hours Conversely, melatonin appears to produce significantly greater, or exaggerated hypnotic effects during daytime hours or times not normally associated with sleep and endogenous melatonin secretion., as found in Tzischinsky and Lavie's "*Melatonin Possesses Time-Dependant Hypnotic Effects*" (Sleep 1994;17:638–45). This may explain reports in some studies of lingering sleep-related measures when melatonin is administered during the day, without the opportunity for sleep which would discharge the sleep drive post melatonin administration. [Dollins, Lynch, Wurtman, Deng, Kischka, Gleason, Lieberman "*Effect of Pharmacological Daytime Doses of Melatonin on Human Mood and Performance*" (Physiol Behav 1993; 53:153–60) "*Effect of Inducing Nocturnal Serum Melatonin Concentrations in Daytime Sleep*" (Dollins, Zhdanova, Wurtman, Lycnch, Deng Proc. Natl Acad Sci USA 1994;91:1824–8); and "*Effect of Daytime Oral Melatonin Administration on Neurobehavioral Performance n Humans*" (Rogers, Kennaway, Dawson *J Pineal Res* 1998; 25:47–53) along with a host of other similar studies.

Many other studies show that, even with some degree of residual sleepiness after melatonin administration with no opportunity for sleep discharge (at doses up to a total of 240 mg. over 2 hours), few if any significant decrements in performance are observed over a wide array of performance tasks such as simulated driving performance (Suhner, Schlagenhauf, Tschopp, Hauri-Bionda, Freidrich-Koch, and Steffen, "*Impact of Melatonin on Driving Performance*" J Travel Med 1998; 5:7–13) and other cognitive performance, memory, visual sensitivity, tracking, time reaction, and vigilance tasks (Lieberman, Waldhauser, Garfield, Lynch, and Wurtman, "*Effects of Melatonin on Mood and Performance*" Brain Res 1984323:201–7; Dawson, Encel, "*Melatonin and Sleep in Humans*" J Pineal Res 1993; 15:1–12; Von Gizycki, et al, "*The Effect of Melatonin on Performance in a Visal Vigilance Task*" Sleep Res 1993; 26:132; and Slotten, "*Does Melatonin Have an Effect on Cognitive Performance?*" Psychoneuroendocrinology 1996; 21:673–80.)

Given the above, it is clear that a need exists for a remedy which can be taken once sleeplessness has been experienced (after retiring to bed). Melatonin has been widely researched and has been found to have a very short half-life and to be exceedingly safe, even at very high dosage levels. Low pharmacological doses of melatonin (from 1.0 and higher) have been found to be reliably effective in promoting sleep. Once the sleep drive has been discharged, unlike the medications currently used to treat sleeplessness, there is little or no residual sleepiness. A number of studies have indicated no significant decrement in broad range of performance tasks following administration of melatonin (and improvement in some performance tasks in some cases.)

OBJECTS OF THE INVENTION

It is among the objects of the present invention to provide a treatment for sleeplessness which can be administered only when needed without taking the remedy in the expectation of needing it.

It is another object of the invention to provide a treatment for sleeplessness which can be taken in the middle of the night without having hangover effects upon awakening in the morning.

Still other objects of the invention will be recognized by those of ordinary skill in the art.

BRIEF SUMMARY OF THE INVENTION

These objects are achieved by administering melatonin in low pharmacologic doses of about 1.0 mg to about 3.0 mg to a patient suffering from sleeplessness at a time period after bedtime until at least 1 hour before the patient intends to wake up in the morning.

BRIEF DESCRIPTION OF THE DRAWING

Not Applicable

DETAILED DESCRIPTION OF THE INVENTION

The present invention is a method of treating sleeplessness in a human comprising administering to said human suffering from said sleeplessness an effective sleep-inducing amount of not greater than about 5 mg of melatonin or a pharmaceutically acceptable salt thereof, said administration being at a point in time after said human attempts to go to sleep until no less than 1 hour prior to said patient's desired awakening time.

For purposes of this invention, sleeplessness is generally a condition that will be subjective to the individuals who will be taking advantage of the invention. The subject will generally attempt to go to sleep at a particular time. After some period of time (a first time period), generally of (but not limited to) at least 15 minutes, whether not falling asleep at all, or drifting in and out of a sleep state, the subject feels that he or she is not falling asleep as desired, and considers that he or she is having an episode of sleeplessness. Similarly, on awakening during the subject's ordinary sleep period (one that is ordinary or typical for the subject at hand in the subject's own estimation) and failing to be able to fall asleep again within a reasonable period of time (a second time period, again, within the subject's own subjective estimation, usually but not limited to, at least 15 minutes). In both cases, the term "suffering from sleeplessness" includes those individuals who desire to quickly fall into a state of sleep.

Generally, the time period for administration of melatonin within the present invention is from the point where one has recognized or believes that one is having an episode of sleeplessness until an amount of time (a third time period) prior to the subject's intended time for awakening. This third time period is generally, but not limited to, not less than one hour, prior to the subject's intended time for awakening. For example, the subject may take the melatonin dose at any time point earlier in the night such as at least 1.5, 2, 2.5, 3, 3.5, 4, or more hours (or any interval between those stated here) prior to the subject's desired awakening time.

The effective sleep-inducing amount of melatonin is preferably about 0.1 mg to about 10 mg, preferably at least about 0.3 mg, more preferably at least about 0.5 mg, even more preferably at least about 1 mg, still more preferably at least about 1.25 mg, most preferably at least about 1.5 mg while preferably not more than about 7.5 mg, more preferably not more than about 5 mg, more preferably not more than about 4.5 mg. A fairly typical dose for a subject would be about 1.5 mg; however, a dose of 3.0 mg, or 4.5 mg may be used as well. Each subject can determine the individual dose for himself or herself based on the subjects own personal reaction to an initial dose of melatonin in accordance with the present invention.

Melatonin is commercially available in a variety of dosage ranges, including 1.5 mg per dosage unit. However, none of the products currently available, to the present inventor's knowledge, have administration instructions that include administering melatonin after attempting to go to sleep or administering melatonin after awakening during a typical sleep period and not being able to go back to sleep.

Melatonin may be administered orally, parenterally (e.g., intracisternally, subcutaneously, intraperitoneally), rectally, transdermally, or nasally, in any suitable dosage form, including capsules, softgels, ordinary or quick dissolve tablets, powders, nasal sprays, sublingual forms, transdermal patches, etc., although instant dissolve tablets or softgels are preferred for their fast delivery of melatonin.

The dosage forms will generally have, in addition to melatonin, a suitable carrier therefore and may have additional formulation excipients generally known in the art. Furthermore, while it is preferable for there to be no other sleep-inducing agents present in the formulation, additional ingredients may be optionally present, if desired. Generally, if ingredients with sleep-inducing properties are present, they will be used in amounts which would be near the minimum or below the therapeutic level for such other active, in order to keep the product from resulting in sleepiness after awakening.

Inactive materials for formulating the melatonin into suitable dosage forms are well know in the art and include, without limitation, carriers, binders, disintegrants, processing aids, lubricants, coating materials, etc. Those of ordinary skill in the art will readily know how to formulate the melatonin into suitable dosage forms, whether alone, or together with other ingredients.

EXAMPLES

The following examples exemplify, but do not limit, the present invention.

Example 1

Melatonin 1.5 mg capsules are administered to subjects having difficulty falling asleep after one hour of trying to fall asleep at their normal bedtime. The subjects fall asleep within 20 minutes and sleep through the night. On awakening, the subjects are alert, without any decrement in faculties.

Example 2

Subjects are those who awake at about midway during their normal sleep period and once awake have trouble falling back asleep. After 15 minutes of trying to fall back asleep, the subjects are given melatonin 1.5 mg capsules. The subjects fall asleep within 20 minutes and sleep through the remainder of the night, awakening 3–4 hours later. The subjects are refreshed, and not sleepy or drowsy.

I claim:

1. A method of treating sleeplessness in a human comprising administering to said human suffering from said sleeplessness an effective sleep-inducing amount of not greater than about 10 mg of melatonin or a pharmaceutically acceptable salt thereof, said administration being at a point in time from (a)(i) after said human has attempted to go to sleep and has failed to go to sleep, or (ii) after said human has awakened from sleep and is unable to return to sleep until (b) no less than one hour prior to said patient's desired awakening time, said administration being while said patient is awake and desires to fall asleep.

2. The method of claim 1 wherein said effective amount is from about 0.1 mg to about 10 mg.

3. The method of claim 1 wherein said effective amount is from about 0.3 mg to about 7.5 mg.

4. The method of claim 1 wherein said effective amount is from about 0.5 mg to about 5 mg.

5. The method of claim 1 wherein said effective amount is from about 1.5 mg to about 4.5 mg.

6. The method of claim 1 wherein said effective amount is about 1.5 mg, about 3 mg, or about 4.5 mg.

7. The method of claim 1 wherein said effective amount is about 1.5 mg.

8. The method of claim 1 wherein said point in time is beyond said patient's bedtime and is at least ¼ hour after said patient has attempted to go to sleep.

9. The method of claim 1 wherein said point in time is beyond said patient's bedtime and is at least ½ hour after said patient has attempted to go to sleep.

10. The method of claim 1 wherein said point in time is beyond said patient's bedtime and is at least 1 hour after said patient has attempted to go to sleep.

11. The method of claim 1 wherein said melatonin or pharmaceutically acceptable salt thereof is administered after said patient has awoken during said patient's intended sleep period.

12. The method of claim 1 wherein said melatonin or pharmaceutically acceptable salt thereof is administered no less than 2 hours prior to said patient's desired awakening time.

13. The method of claim 1 wherein said melatonin or pharmaceutically acceptable salt thereof is administered no less than 3 hours prior to said patient's desired awakening time.

14. The method of claim 1 wherein said melatonin or pharmaceutically acceptable salt thereof is administered no less than 4 hours prior to said patient's desired awakening time.

15. A combination article of manufacture comprising an oral dosage form of melatonin or a pharmaceutically acceptable salt thereof in an effective sleep-inducing amount of up to about 10 mg per dosage unit together with labeling therefore, said labeling having an indication for acute treatment of sleeplessness with administration of said oral dosage form to be to a patient after said patient has (a)(i) attempted to sleep yet has experienced sleeplessness or (ii) has awakened from sleep and has been unable to return to sleep, but (b) no less than 1 hour before said patient's intended awakening time said administration being while said patient is awake and desires to fall asleep or upon awakening from sleep and desiring to return to sleep.

* * * * *